US00PP12117P2

(12) United States Plant Patent
Fransen

(10) Patent No.: US PP12,117 P2
(45) Date of Patent: Oct. 2, 2001

(54) HOSTA PLANT NAMED 'PARADISE POWER'

(75) Inventor: Marco Fransen, Ter Aar (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/642,990

(22) Filed: Aug. 22, 2000

(51) Int. Cl.[7] ..... A01H 5/00
(52) U.S. Cl. ..... Plt./353
(58) Field of Search ..... Plt./353

(56) References Cited

PUBLICATIONS

UPOV ROM GTITM Computer Database, GTI JOUVE Retrieval Software, citations for 'Paradise Power' Feb. 2001.

*Primary Examiner*—Bruce R. Campell
*Assistant Examiner*—Wendy C. Baker
(74) *Attorney, Agent, or Firm*—C. A. Whealy

(57) ABSTRACT

A distinct cultivar of Hosta plant named 'Paradise Power', characterized by its golden yellow leaf color; relatively compact plant habit; and lavender-colored flowers that are positioned above the foliage on strong and erect scapes.

2 Drawing Sheets

BACKGROUND OF THE INVENTION

The present Invention relates to a new and distinct cultivar of Hosta plant, botanically known as Hosta hybrid, and hereinafter referred to by the cultivar name Paradise Power.

The new Hosta was discovered by the Inventor in a controlled environment in Ter Aar, The Netherlands, as a whole plant mutation of the Hosta hybrid cultivar Sun Power, not patented, in 1994. Plants of the cultivar Sun Power have solid golden yellow-colored leaves whereas plants of the new Hosta have golden yellow-colored leaves with green margins.

Asexual reproduction of the new cultivar by divisions harvested in Ter Aar, The Netherlands, has shown that the unique features of this new Hosta are stable and reproduced true to type in successive generations.

SUMMARY OF THE INVENTION

Plants of the cultivar Paradise Power have not be observed under all possible environmental conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Paradise Power'. These characteristics in combination distinguish 'Paradise Power' as a new and distinct cultivar:

1. Golden yellow leaf color with green margins.
2. Relatively compact plant habit.
3. Lavender-colored flowers that are positioned above the foliage on strong and erect scapes.

BRIEF DESCRIPTION OF THE PHOTOGRAPHS

The accompanying colored photographs illustrate the overall appearance of the new Hosta, showing the colors as true as it is reasonably possible to obtain in colored reproductions of this type. Colors in the photographs may differ slightly from the the color values cited in the detailed botanical description which more accurately describe the actual colors of the new Hosta.

The photograph on the first sheet comprises a side perspective view of a typical flowering plant of 'Paradise Power' grown in a container.

The photograph at the top of the second sheet is a close-up view of a typical flowering stem of 'Paradise Power'.

The photograph at the bottom of the second sheet is a close-up view of the upper surface of a typical leaf of 'Paradise Power'.

DETAILED BOTANICAL DESCRIPTION

In the following description, color references are made to The Royal Horticultural Society Colour Chart except where general terms of ordinary dictionary signifcance are used. Plants used for the following description were about 40 weeks old and grown in 17-cm containers under field conditions which closely approximate commercial production conditions during the spring and summer in Ter Aar, The Netherlands.

Botanical classification: Hosta hybrid cultivar Paradise Power.

Parentage: Whole plant mutation of Hosta hybrid cultivar Sun Power, not patented.

Propagation:

*Type cutting.*—By divisions.

*Rooting time.*—Divisions harvested in the spring develop roots in about 20 days.

*Root description.*—Fleshy.

Plant description:

*Form.*—Perennial flowering plant; initially upright becoming outwardly arching as leaves develop; inverted triangle. Moderately clumping. Appropriate for 17-cm containers.

*Crop time.*—After rooting, about 40 weeks are required to produce finished flowering plants in 17-cm containers.

*Plant height.*—From soil level to top of leaf plane: About 20 cm. From soil level to top of flowering stems: About 60 cm.

*Plant diameter.*—About 30 cm.

*Vigor.*—Moderately vigorous.

*Foliage description.*—Leaves basal, simple, generally symmetrical, and long-persisting. Length: About 14 cm. Width: About 6 cm. Shape: Lanceolate. Apex: Acuminate. Base: Cuneate. Margin: Entire. Texture: Glabrous, slightly glossy. Petiole: Length: About 6.5 cm. Diameter: About 7 mm. Color: Young foliage, upper surface: 145A to 151A; margins, close to 144A. Young foliage, lower surface: 144C to 145B; margins, close to 144A. Mature foliage, upper surface: 151B to 151C; margins, close to 144A; veins, 141D. Mature foliage, lower surface: 145A to 151A; margins, close to 144A; veins, 145A to 151A. Petiole color: Distally, 151A to 151B; towards base, 144A.

Flower description:

*Appearance.*—Single campanulate to funnelform flowers with fused perianth arranged on one-sided racemes. Flowering stems arise from leaf axils. Typically two flowering stems per plant. Flowers persistent.

*Quantity of flowers.*—About 15 flowers per raceme.

*Natural flowering season.*—Summer in the Netherlands; flowering continuous.

*Fragrance.*—Not fragrant.

*Flower longevity.*—About 4 to 7 days.

*Flower size.*—Length: About 4.5 cm. Diameter: About 3 cm.

*Flower buds* (*about 4 days before opening*).—Length: About 2.4 cm. Diameter: About 8 mm. Shape: Oblanceolate. Color: 76A to 76B.

*Perianth.*—Arrangement: Three interior and three exterior tepals; fused. Tepal length: About 3.7 cm. Tepal width: About 9 mm. Tepal shape: Lanceolate; apex, acute; margin, entire. Tepal texture: Smooth; glabrous. Tepal color: When opening, upper and lower surfaces: 76A to 76B. Fully opened, upper and lower surfaces: 76B to 76C, fading 76C to 76D.

*Floral bracts.*—Arrangement: At pedicel base. Length: About 1.9 cm. Width: About 9 mm. Shape: Broadly lanceolate. Color: 141C to 141D.

*Pedicel.*—Length: About 7 mm. Angle: Erect to about 80 to 90° from vertical. Strength: Strong. Color: 76A to 76B with green undertones.

*Scape.*—Length: About 60 cm. Aspect: Mostly upright. Texture: Smooth; slightly glaucous. Color: 141C to 141D.

*Reproductive organs.*—Stamens: Quantity: Six; dorsifixed. Anther size: About 4 by 1 mm. Anther color: 187A. Pollen amount: Scarce. Pistils: Quantity: One. Pistil length: About 3.5 cm. Style length: About 3.4 cm. Style color: 142D. Stigma color: 142D. Ovary color: 138B to 137D or paler.

*Seed description.*—Length: About 4 mm. Diameter: About 1 mm. Color: Close to black.

Disease resistance: Plants of the new Hosta have not been noted to be resistant to pathogens common to Hosta.

It is claimed:

1. A new and distinct cutlivar of Hosta plant named 'Paradise Power', as illustrated and described.

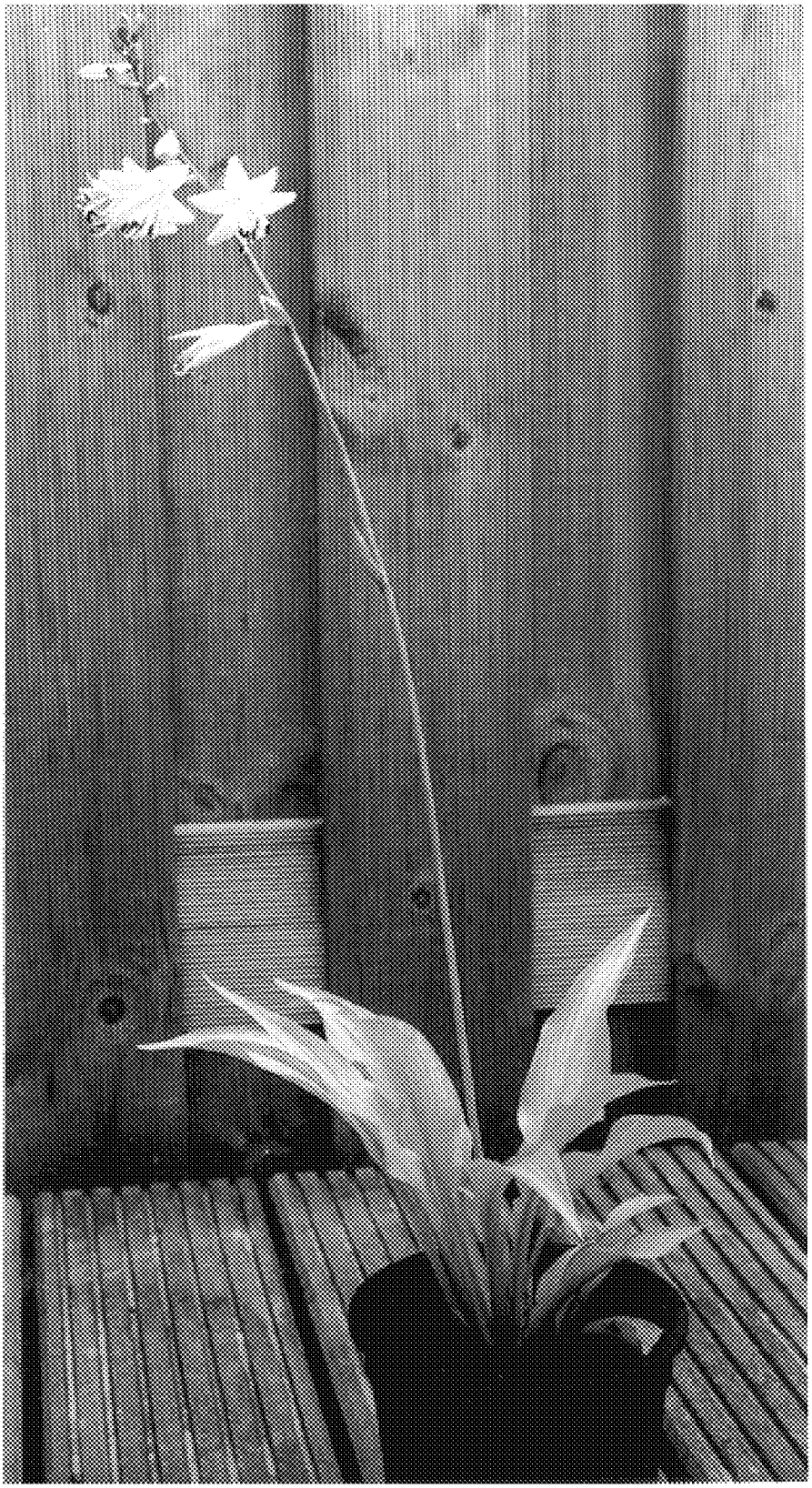

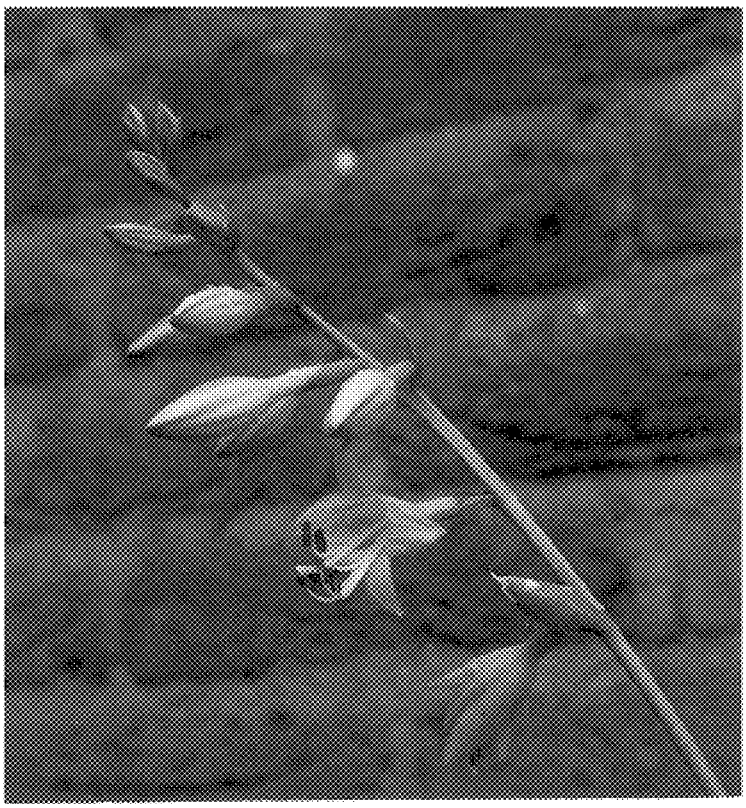
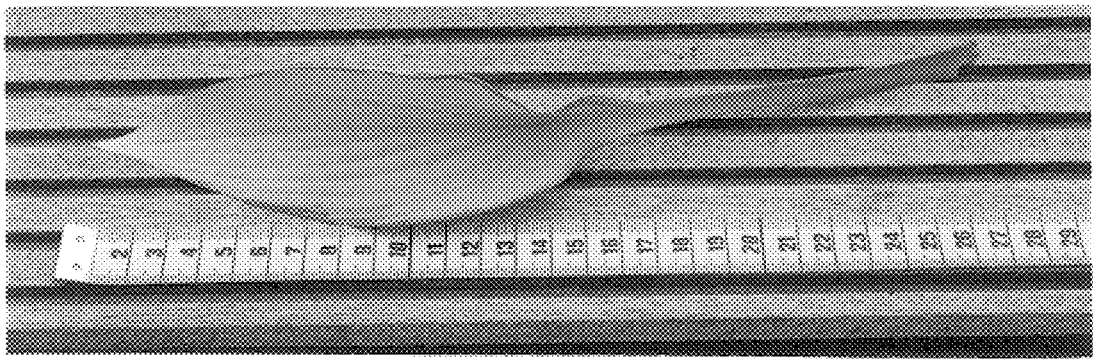

* * * * *